(12) United States Patent
Winter et al.

(10) Patent No.: US 8,598,385 B2
(45) Date of Patent: Dec. 3, 2013

(54) PROCESS FOR THE PREPARATION OF N-VINYLCARBOXAMIDES

(75) Inventors: Manfred Winter, Dittelsheim-Hessloch (DE); Hagen Weigl, Ladenburg (DE); Andreas Kramer, Friedelsheim (DE)

(73) Assignee: BASF SE, Ludwigshafen (DE)

( * ) Notice: Subject to any disclaimer, the term of this patent is extended or adjusted under 35 U.S.C. 154(b) by 220 days.

(21) Appl. No.: 13/139,521

(22) PCT Filed: Dec. 4, 2009

(86) PCT No.: PCT/EP2009/066387
§ 371 (c)(1),
(2), (4) Date: Jun. 14, 2011

(87) PCT Pub. No.: WO2010/072543
PCT Pub. Date: Jul. 1, 2010

(65) Prior Publication Data
US 2011/0245539 A1 Oct. 6, 2011

(30) Foreign Application Priority Data
Dec. 15, 2008 (EP) .................................... 08171677

(51) Int. Cl.
*C07C 231/06* (2006.01)

(52) U.S. Cl.
USPC ........................................................ 564/130

(58) Field of Classification Search
USPC ........................................................ 564/130
See application file for complete search history.

(56) References Cited

FOREIGN PATENT DOCUMENTS

| DE | 1 224 304 | 9/1966 |
| DE | 1 668 038 | 7/1971 |
| EP | 0 184 074 | 6/1986 |
| EP | 0 184 694 | 6/1986 |

OTHER PUBLICATIONS

International Search Report issued Jun. 10, 2010 in PCT/EP2009/066387.
P. Kurtz, et al., "Enamide", Liebigs Ann. Chem., vol. 764, XP-002583721, 1972, pp. 69-93.
International Search Report Issued Jun. 10, 2010 in PCT/EP09/066387 filed Dec. 4, 2009.

*Primary Examiner* — Shailendra Kumar
(74) *Attorney, Agent, or Firm* — Oblon, Spivak, McClelland, Maier & Neustadt, L.L.P.

(57) ABSTRACT

Process for the preparation of N-vinylcarboxamides by pyrolysis of a compound of the formula $$CH_3-CH(CN)-N(R)-CO-R^1 \qquad (I),$$

in which R and $R^1$ are H or $C_1$- to $C_6$-alkyl, in the presence of solids which are doped with alkali metal or alkaline earth metal ions, under reduced pressure at a temperature of from 330 to 750° C. with elimination of hydrogen cyanide, cooling, separation and isolation of the reaction products, a solid arranged in a tubular reactor being treated at a temperature in the range from 0 to 250° C. with a solution of an alkali metal and/or alkaline earth metal base, the solution being discharged, the remaining solvent which adheres to the catalyst thus obtainable being evaporated and said catalyst then being heated to a temperature of at least 380° C. for activation.

20 Claims, No Drawings

PROCESS FOR THE PREPARATION OF N-VINYLCARBOXAMIDES

This application is a National Stage of PCT/EP09/066,387 filed Dec. 4, 2009 and claims the benefit of EP 08171677.1 filed Dec. 15, 2008.

The invention relates to a process for the preparation of N-vinylcarboxamides by pyrolysis of a compound of the formula $$CH_3-CH(CN)-N(R)-CO-R^1 \qquad (I),$$

in which R and $R^1$ are H or $C_1$- to $C_6$-alkyl,
in the presence of solids which are doped with alkali metal or alkaline earth metal ions, under reduced pressure at a temperature of from 330 to 750° C. with elimination of hydrogen cyanide, cooling, separation and isolation of the reaction products.

DE-C 1 224 304 discloses a process for the preparation of N-vinylcarboxamides, such as N-vinylformamide or N-vinylacetamide, by pyrolysis of compounds of the formula I at a temperature in the range from 250 to 750° C. under atmospheric pressure or under reduced pressure in a tubular reactor with elimination of hydrogen cyanide, cooling, separation and isolation of the reaction products. For increasing the size of the reaction surface, the tubular reactor comprises solids, such as quartz fragments, glass, iron, silicon carbide, aluminum fluoride, coke, calcium phosphate or alumina. The hydrogen cyanide forming during the reaction is condensed after the vinylcarboxamides have been separated off.

EP-A 0 184 694 discloses a process for the preparation of reaction products of hydrogen cyanide with bases or carbonyl compounds, the hydrogen cyanide being prepared by pyrolysis of formamide or N-acyl derivatives of 1-amino-1-cyanoethane or the substitution products thereof at from 250 to 650° C. on solids as a catalyst and at a pressure of from 5 to 200 mbar. The pyrolysis gases are cooled under reduced pressure to a temperature in the range from 200 to −10° C. During this procedure, the monomers formed during the pyrolysis and any unconverted starting materials condense. The condensate comprises only small amounts of hydrogen cyanide. The main amount of hydrogen cyanide is subjected under reduced pressure to chemisorption with bases or carbonyl compounds and is discharged in the form of the condensates and let down to atmospheric pressure. In this process, the handling of relatively large amounts of hydrogen cyanide is avoided.

EP-A 0 184 074 discloses a process for the preparation of N-vinylformamide, formylalaninenitrile being pyrolyzed in the presence of solids as a catalyst under reduced pressure at a temperature in the range from 250 to 650° C. Those solids which are stated in the abovementioned DE-C 1 224 304 and also alkali metal and alkaline earth metal carbonates, magnesium oxide, calcium oxide, barium oxide and in particular those catalysts which comprise alkali metal or alkaline earth metal carbonates on α-alumina can be used as a catalyst. These catalysts are prepared by impregnating α-alumina with water-soluble salts, such as calcium acetate, and subjecting it to a thermal treatment. The pyrolysis products substantially comprise N-vinylformamide, hydrogen cyanide and small amounts of unconverted formylalaninenitrile. They are cooled under a pressure of from 10 to 150 mbar to a temperature of from 200 to −10° C. so that substantial separation into N-vinylformamide and hydrogen cyanide takes place, the monomer is isolated from the condensate and the uncondensed hydrogen cyanide is subjected, under a pressure of from 5 to 140 mbar, in approximately molar ratio, to a chemisorption with acetaldehyde at temperatures of from −20 to 30° C. with formation of lactonitrile and is isolated after pressure equilibration with the atmosphere. In this process, the formation of relatively large amounts of free hydrogen cyanide is likewise avoided because it is converted directly into a product which can be handled without danger.

When the process for the preparation of N-vinylcarboxamides by pyrolysis is carried out in practice, there is a decrease in conversion and selectivity with increasing duration of production. The catalyst must then be renewed or reactivated. In the case of tubular reactors, replacement of the catalyst gives rise to considerable expense because such reactors have very many tubes, in general several hundred tubes, which then have to be emptied and refilled. Moreover, during installation and removal of the catalyst, mechanical damage to the catalyst must always be expected. In order to remove carbon-containing deposits from a catalyst, it can be treated within the reactor with a gas comprising oxygen at relatively high temperatures. However, the full activity of the catalyst cannot be restored an arbitrary number of times. Rather, it is then necessary to remove the catalyst and to reactivate it outside the reactor by treatment with an alkali metal base and/or alkaline earth metal base and to subject it to a thermal treatment.

It is the object of the invention to provide a process for the preparation of N-vinylcarboxamides by pyrolysis, it being possible to carry out the activation and reactivation of the catalyst in the reactor in which the pyrolysis takes place.

The object is achieved, according to the invention, by a process for the preparation of N-vinylcarboxamides by pyrolysis of a compound of the formula $$CH_3-CH(CN)-N(R)-CO-R^1 \qquad (I),$$

in which R and $R^1$ are H or $C_1$- to $C_6$-alkyl,
in the presence of solids which are doped with alkali metal or alkaline earth metal ions, under reduced pressure at a temperature of from 330 to 750° C. with elimination of hydrogen cyanide, cooling, separation and isolation of the reaction products, if a solid arranged in a tubular reactor is treated with a solution of an alkali metal base and/or alkaline earth metal base at a temperature in the range from 0 to 250° C., the solution is discharged, the remaining solvent which adheres to the catalyst thus obtained is evaporated and said catalyst is then heated to a temperature of at least 380° C. for activation.

The compounds of the formula I are disclosed, for example, in EP-A 0 184 694 mentioned in connection with the prior art, cf. column 2, line 40 to column 3, line 23. A preferably used compound of the formula I is formylalaninenitrile (formula I where R═H and $R^1$═H), in order to prepare N-vinylformamide therefrom by pyrolysis. Also of interest are those compounds in the formula I, in which R is H and $R^1$ is $CH_3$, for the preparation of N-vinylacetamide, R is H and $R^1$ is $C_2H_5$, for the preparation of N-vinylpropylamide, R is $CH_3$ and $R^1$ is H, for the preparation of N-vinyl-N-methylformamide and R is $CH_3$ and $R^1$ is $CH_3$, for the preparation of N-vinyl-N-methylacetamide.

The pyrolysis is effected in the presence of solids which are doped with alkali metal and/or alkaline earth metal ions. Suitable solids are mentioned, for example, in DE-C 1 224 304, column 2, lines 16 to 24, and in EP-A 0 184 074, column 1, lines 52 to 66. For example, silicon dioxide, silicon carbide, active carbon, calcium phosphate, alumina, titanium dioxide and aluminum oxides are suitable. A particularly preferably used solid is α-alumina. In principle, all porous solids are suitable as a support for the catalyst. The solids are arranged, for example, in the form of strands, spheres, tubes, moldings or lamelae in the tubular reactor.

The tubular reactor may consist of a single tube or of a multiplicity of tubes. Such reactors may have, for example, from 1 to 35000 tubes, in general from 5 to 10000 tubes, in particular up to not more than 3000 or up to 5000 tubes, it being possible for the tube diameter to vary in a range from 0.3 cm to 25 cm, in general from 1 cm to 14 cm. The tubular reactor can be heated electrically, with superheated steam, recycled gas or circulating gas or with the aid of a salt bath.

To ensure that the solids are subjected to as little mechanical stress as possible, the treatment with alkali metal base and/or alkaline earth metal bases is effected only after installation of the solids in the tubular reactor. For this purpose, they are brought into contact at a temperature in the range from 0 to 250° C. with a solution of an alkali metal base and/or alkaline earth metal base. Aqueous solutions are preferably used for this purpose. However, water-miscible products, such as dimethylformamide, tetrahydrofuran, dioxane, methanol, ethanol, propanol, isopropanol, butanol, cyclohexanol, alkylene glycols, polyalkylene glycols, alkoxylated alcohols, alkoxylated amines and mixtures thereof with one another or with water, can also be used as solvents for the bases. Examples of alkylene glycols are ethylene glycol, 1,2-propylene glycol, 1,3-propylene glycol, 1,2-butylene glycol, 1,4-butylene glycol and neopentyl glycol. Further suitable solvents are, for example, polyalkylene glycols, such as diethylene glycol, triethylene glycol, tetraethylene glycol and ethoxylation products of polyhydric alcohols, such as propylene glycol, glycerol, pentaerythritol or trimethylolpropane. The degree of ethoxylation is preferably chosen so that the resulting ethoxylation products have a boiling point of not more than 350° C. at a pressure of 50 mbar. If the catalyst arranged in the reactor has a temperature which is above the boiling point of the solvent, the treatment of the catalyst with solutions of bases is effected under elevated pressure. This is, for example, the pressure which is established at the respective temperature. The treatment of the catalyst is preferably effected at a temperature of from 10 to 80° C. with an aqueous solution of an alkali metal base and/or of an alkaline earth metal base under atmospheric pressure.

Suitable alkali metal base and/or alkaline earth metal bases are, for example, all water-soluble salts and bases of alkali metals and alkaline earth metals, such as, in particular, sodium hydroxide, potassium hydroxide, calcium hydroxide, strontium hydroxide, barium hydroxide, calcium acetate, calcium formate, barium formate, magnesium acetate, sodium bicarbonate, potassium bicarbonate, sodium carbonate, potassium carbonate, sodium acetate and potassium acetate. The aqueous solutions with which the solids are treated in the reactor have, for example, a concentration of at least 5% by weight of a base or of a salt upto the respective saturation concentration. The concentration of a base or of a salt in the aqueous treatment solution is in general from 1 to 50, in particular from 30 to 45, % by weight.

After the treatment of the solids with a solution of an alkali metal base and/or alkaline earth metal base, the solution is discharged. Thereafter, the remaining solvent which adheres to the solids treated in this manner in the reactor is evaporated and in this way a porous support doped with an alkali metal and/or alkaline metal base is obtained as catalyst. High-boiling solvents, such as glycols or polyalkylene glycols, which still wet the catalyst after discharge of the solvent are preferably removed by heating the catalyst to temperatures up to 270° C. under reduced pressure, e.g. at from 10 to 100 mbar.

The solid introduced into the tubular reactor is preferably treated with an aqueous solution of sodium carbonate or potassium carbonate. A particularly preferably used catalyst is prepared by treating α-alumina with an aqueous solution of sodium carbonate or potassium carbonate. The drying of the impregnated solids is initially effected, for example, by passing an inert gas stream through the reactor and increasing the temperature of the inert gas stream continuously or stepwise. However, the reactor can also be heated from the outside and an inert stream additionally passed through the catalyst load. Suitable inert gases are, for example, superheated steam, air or nitrogen. If the catalyst is treated with an aqueous solution of an alkali metal or alkaline earth metal base, said catalyst is first dried at a temperature up to 200° C., preferably in the temperature range from 160 to 195° C. The drying process is complete when virtually no more steam is detectable in the exit gas. After the drying, the impregnated solids, i.e. the catalysts, are heated to a temperature of at least 380° C., in general at least 430° C., in particular at least 450° C., for activation. The activation of the catalyst is preferably carried out in the temperature range from 450 to 550° C.

The activation of the catalyst is effected as a rule at a temperature which is at least 10° C. above the temperature at which the pyrolysis of the compound of the formula I is carried out. After drying, the catalyst is preferably heated in the tubular reactor to a temperature which is at least 50° C. above the temperature at which the pyrolysis is subsequently carried out. The heating of the catalyst lasts, for example, for from 5 to 72 hours.

If a porous solid, in particular α-alumina, has been treated with an aqueous solution of sodium carbonate and/or potassium carbonate or an aqueous solution of another carbonate, the progress of the heating of the catalyst can be monitored with the aid of an analysis of the exit gas. For example, the catalyst is heated in the tubular reactor at a temperature of at least 380° C. and the $CO_2$ content of the exit gas is continuously measured. The heating of the catalyst is complete as soon as virtually no more $CO_2$ is detectable in the exit gas. The catalyst is then cooled to the temperature at which the pyrolysis is subsequently carried out.

The pyrolysis of the N-vinylcarboxamides is effected under reduced pressure. This substantially suppresses or prevents an undesired polymerization and/or decomposition of the resulting monomers. During the pyrolysis, the pressures are in the range of, for example, from 1 to 500 mbar, preferably in the range from 5 to 200 mbar. The temperatures during the pyrolysis are, for example, in the temperature range from 330 to 750° C., preferably from 350 to 550° C. Suitable reaction conditions are described in detail, for example, in DE-C 1 224 304, EP-A 0 184 074, column 1, line 51 to column 3, line 53, and EP-A 0 184 694, column 2, line 34 to column 6. The statements made there apply in a corresponding manner to processes according to the invention. The substances forming during the pyrolysis, which are gaseous under the reaction conditions, are cooled so that the monomers formed in each case condense. They are removed continuously or batchwise, after pressure equilibration with the atmosphere, freed from small amounts of hydrogen cyanide and purified. The hydrogen cyanide can, if desired, be obtained as a liquid by cooling to low temperatures and pressure equilibration with atmospheric pressure. For safety reasons, however, the chemisorption of the hydrogen cyanide on bases or carbonyl compounds, as described in the abovementioned EP applications, is preferred. Pyrolysis and chemisorption are carried out continuously.

The activated catalyst prepared by the process according to the invention has, for example, an on-stream time of at least 12 weeks. As soon as the selectivity of the catalyst and/or the conversion decrease, the catalyst must be regenerated. For example, the catalyst is regenerated as soon as the conversion has fallen to a value of 80%, in general 90%. For this purpose, as a rule, a procedure is firstly adopted in which the carbon-containing deposits on the catalyst are oxidized in an inert gas stream, such as superheated steam, with supply of oxygen. If such activation of the catalyst is no longer possible because the alkali metal concentration on the catalyst is no longer sufficient, the production of N-vinylcarboxamides is stopped and the catalyst in the tubular reactor is cooled to a temperature at which the catalyst regeneration according to the invention is then effected by treatment with a solution of an alkali metal base and/or alkaline earth metal base.

If, for example, the reactor is heated with the aid of a salt bath, it can be cooled for activation of the catalyst, for example to a temperature in the range from 200 to 250° C., and—if it is designed for higher pressures—the catalyst can then be treated with an aqueous solution of an alkali metal base and/or alkaline earth metal base under pressure without discharging the salt bath. However, the salt bath is then likewise cooled to a temperature in said range. The treatment of a catalyst can, however, also be effected in the temperature range from 200 to 250° C. under atmospheric pressure if a solvent or a solvent mixture which boils above 250° C., preferably above 300° C., at atmospheric pressure is used for the bases. After the treatment with a solution of a base, the remaining solvent which wets the catalyst is removed and the catalyst is activated in the tubular reactor by heating to a temperature of at least 380° C. However, the reactor can also be heated, for example, via another heat-transfer medium, such as oil, or directly electrically or with hot gases.

If it is intended to carry out the treatment of the catalyst with a solution of a suitable base at temperatures below the boiling point of the solvent, for example in the range from 10 to 80° C., the catalyst is cooled in the tubular reactor to a temperature in this range. Cooling can be carried out in two stages by first cooling the catalyst in the reactor to a temperature in the range from 200 to 250° C. under atmosphere pressure and then cooling it under reduced pressure in an inert gas stream to a temperature below 100° C. For example, air, nitrogen or steam can be used as inert gas. For example, for drying of the catalyst, steam under reduced pressure (e.g. at from 10 to 700 mbar, preferably from 20 to 100 mbar, particularly preferably from 30 to 50 mbar) can be passed through the reactor. After the pressure equilibration with the atmosphere and impregnation of the catalyst with a solution of a base, the solution of the base is discharged from the tubular reactor and the remaining solvent is removed by heating the catalyst thus treated in the tubular reactor. In addition, it is also possible to pass an inert gas stream through the reactor and/or to apply reduced pressure, e.g. pressures of from 10 to 500 mbar. In order finally to activate the catalyst, it is heated in the tubular reactor to a temperature of at least 380° C.

While, according to the prior art, the catalyst has to be removed from the tubular reactor and impregnated in a separate apparatus and, if desired, also heated, in the process according to the invention it can remain in the reactor for activation and regeneration. This results in a substantial time saving for the production of N-vinylcarboxamides compared with the known procedure. Moreover, mechanical destruction of the catalyst owing to removal and installation measures is avoided. After the activation, the catalyst immediately has good conversion and selectivity values.

The process according to the invention is in particular industrially important for the preparation of N-vinylformamide, which is obtainable by pyrolysis of the compound of the formula I where R═H and $R^1$═H (N-formylalaninenitrile). For example, polymers which, if desired after complete or partial hydrolysis, are used as thickening agents, flocculants and retention aids in the production of paper are prepared from N-vinylformamide.

EXAMPLE

In the preparation of N-vinylformamide by the process of EP-A 0 184 074, carbon-containing deposits which reduced the conversion and led to a pressure drop in the plant formed on the catalyst and on the inner walls of the reactor, which consisted of a reactor tube having a nominal diameter of 80 mm. The catalyst consisted of alumina which was activated with potassium ions. The activity also decreased as a result of a loss of potassium as an active component in the catalyst material. First, the carbon-containing deposits on the catalyst and in the reactor were removed by passing in 200 l/h of nitrogen and 1 kg/h of superheated steam at a temperature of 530° C. and subsequently air was mixed into the gas stream under controlled conditions. After 15 hours altogether the $CO_2$ content in the exit gas was 0.05% by volume. Catalyst and reactor had been virtually completely freed from carbon-containing deposits after this time.

Thereafter, the reactor temperature was reduced to 205° C. and the salt melt was then discharged into a thermostated collecting container. The temperature of the reactor was further reduced by passing over initially 1300 l/h of cold air and then, after the temperature had fallen to 160° C., with 1 kg/h of steam. On reaching 120° C., a vacuum of 100 mbar was applied to the reactor system and was then gradually reduced to 50 mbar (abs), the temperature was then reduced to about 30° C., and the bottom reactor discharge was then closed. The reactor was filled with a 39.9% by weight aqueous solution comprising potassium carbonate until all catalyst bodies were covered. This solution remained in the reactor for 9 hours and was then discharged.

The catalyst was then dried by passing over 1300 l/h of air-heated to 230° C. by means of an external air heater. Thereafter, the reactor space for the heat-transfer medium was filled again with the salt melt and heated further. A stream of 1300 l/h of air was passed over the catalyst and the carbon dioxide concentration was measured. After an initial increase in the concentration from a temperature of about 350° C., said concentration decreased again to the original blank value of 0.05% by volume on further heating. When the reactor had reached a temperature of 550° C., the heating was terminated and the reactor was cooled to 330° C. The pressure in the reactor was then reduced to 10 mbar. 2 kg of formylalaninenitrile per hour were then passed in vapor form through the tubular reactor. The reaction gas formed was quenched by means of cooled liquid reaction product, the N-vinylformamide formed from the formylalaninenitrile being condensed. It was discharged continuously and purified by distillation. The remaining proportion of gas, which substantially comprised hydrogen cyanide, was passed under reduced pressure through acetaldehyde in order to remove hydrogen cyanide with the aid of chemisorption.

We claim:
1. A process for preparing at least one N-vinylcarboxamide, the method comprising:
pyrolyzing a compound of formula

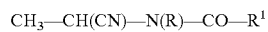     (I), wherein R and $R^1$ are H or $C_1$- to $C_6$-alkyl, in the presence of at least one solid which is a catalyst and is doped with at least one alkali metal or alkaline earth metal ion, under reduced pressure at a temperature of from 330 to 750° C.;

eliminating hydrogen, cyanide; cooling an intermediate product obtained after the eliminating;

separating and isolating at least one reaction product, wherein the at least one solid is arranged in a tubular reactor and treated with a solution of at least one selected from the group consisting of an alkali metal base and alkaline earth metal base at a temperature in a range from 0 to 250° C., the solution is discharged to give the catalyst, remaining solvent which adheres to the catalyst thus obtained is evaporated and the catalyst is then heated to a temperature of at least 380° C. for activation.

2. The process to of claim 1, wherein, after evaporation of the solvent, the catalyst is heated in the tubular reactor to a temperature which is at least 10° C. above a temperature at which the pyrolyzing is subsequently carried out.

3. The process of claim 1, wherein, after evaporation of the solvent, the catalyst is heated in the tubular reactor to a temperature which is at least 50° C. above a temperature at which the pyrolyzing is subsequently carried out.

4. The process of claim 1, wherein the catalyst is a porous support doped with at least one selected from the group consisting of an alkali metal base and an alkaline earth metal base.

5. The process of claim 1, wherein the solid is treated in the tubular reactor with an aqueous solution of sodium carbonate or potassium carbonate.

6. The process of claim 5, wherein the catalyst is heated in the tubular reactor at a temperature of at least 380° C., and wherein a $CO_2$ content of an exit gas is continuously measured and the heating terminated as soon as virtually no more $CO_2$ is detectable in the exit gas, and the catalyst is then cooled to a temperature at which the pyrolyzing is subsequently carried out.

7. The process of claim 1, wherein the pyrolyzing is carried out at a temperature in a range from 350 to 550° C.

8. The process of claim 1, wherein the compound of formula I comprises N-formylalaninenitrile.

9. The process of claim 2, wherein, after evaporation of the solvent, the catalyst is heated in the tubular reactor to a temperature which is at least 50° C. above a temperature at which the pyrolyzing is subsequently carried out.

10. The process of claim 1, wherein the catalyst is a porous support doped with at least one alkali metal base.

11. The process of claim 1, wherein the catalyst is a porous support doped with at least one alkali metal base and at least one alkaline earth metal base.

12. The process of claim 2, wherein the catalyst is a porous support doped with at least one selected from the group consisting of an alkali metal base and an alkaline earth metal base.

13. The process of claim 3, wherein the catalyst is a porous support doped with at least one selected from the group consisting of an alkali metal base and an alkaline earth metal base.

14. The process of claim 2, wherein the solid is treated in the tubular reactor with an aqueous solution of sodium carbonate or potassium carbonate.

15. The process of claim 3, wherein the solid is treated in the tubular reactor with an aqueous solution of sodium carbonate or potassium carbonate.

16. The process of claim 4, wherein the solid is treated in the tubular reactor with an aqueous solution of sodium carbonate or potassium carbonate.

17. The process of claim 2, wherein the pyrolyzing is carried out at a temperature in a range from 350 to 550° C.

18. The process of claim 3, wherein the pyrolyzing is carried out at a temperature in a range from 350 to 550° C.

19. The process of claim 4, wherein the pyrolyzing is carried out at a temperature in a range from 350 to 550° C.

20. The process of claim 6, wherein the pyrolyzing is carried out at a temperature in a range from 350 to 550° C.

* * * * *